(12) United States Patent
Auclair et al.

(10) Patent No.: US 12,219,974 B2
(45) Date of Patent: Feb. 11, 2025

(54) PROBIOTIC FOR POULTRY OR CUD-CHEWING ANIMALS

(71) Applicant: LESAFFRE ET COMPAGNIE, Paris (FR)

(72) Inventors: Eric Auclair, Avelin (FR); Christine Julien, Sepx (FR); Jean-Philippe Marden, Labege (FR)

(73) Assignee: LESAFFRE ET COMPAGNIE, Paris (FR)

( * ) Notice: Subject to any disclaimer, the term of this patent is extended or adjusted under 35 U.S.C. 154(b) by 915 days.

(21) Appl. No.: 17/055,354

(22) PCT Filed: May 14, 2019

(86) PCT No.: PCT/FR2019/051097
§ 371 (c)(1),
(2) Date: Nov. 13, 2020

(87) PCT Pub. No.: WO2019/220052
PCT Pub. Date: Nov. 21, 2019

(65) Prior Publication Data
US 2021/0219568 A1    Jul. 22, 2021

(30) Foreign Application Priority Data
May 15, 2018   (FR) ...................... 1854046

(51) Int. Cl.
A23K 10/18    (2016.01)
A23K 50/10    (2016.01)
A23K 50/75    (2016.01)
C12N 1/18     (2006.01)
C12R 1/865    (2006.01)

(52) U.S. Cl.
CPC .............. *A23K 10/18* (2016.05); *A23K 50/10* (2016.05); *A23K 50/75* (2016.05); *C12N 1/185* (2021.05); *C12R 2001/865* (2021.05)

(58) Field of Classification Search
None
See application file for complete search history.

(56) References Cited

U.S. PATENT DOCUMENTS

| | | | |
|---|---|---|---|
| 4,318,991 A | 3/1982 | Hill | |
| 2002/0146399 A1 | 10/2002 | Raczek | |
| 2009/0202678 A1* | 8/2009 | Sampsonis | A23L 33/14 426/62 |
| 2016/0312245 A1 | 10/2016 | Bavouzet et al. | |
| 2019/0241863 A1 | 8/2019 | Bartolucci et al. | |

FOREIGN PATENT DOCUMENTS

| | | |
|---|---|---|
| CN | 101463329 A | 6/2009 |
| CN | 104988089 A | 10/2015 |
| CN | 105146205 A | 12/2015 |
| FR | 2909685 A1 | 6/2008 |
| WO | 97/00017 A1 | 1/1997 |
| WO | 9951746 A1 | 10/1999 |
| WO | WO-2012110711 A1 * | 8/2012 ........... A21D 13/062 |

OTHER PUBLICATIONS

Colavizza et al. EP 1559322 Machine Translation (Year: 2005).*
Han CN 107843322 Mar. 2018 (Year: 2018).*
International Search Report issued on Sep. 18, 2019 in corresponding International application No. PCT/FR2019/051097; 4 pages.
K.-L. Chen et al. "Effects of *Bacillus subtilis* var. *natto* and *Saccharomyces cerevisiae* mixed fermented feed on the enhanced growth performance of broilers" Poultry Science, Oxford, vol. 88, No. 2, Feb. 1, 2009 (Feb. 1, 2009), pp. 309-331, 7 pgs.
W. Chen et al. "Effects of *Bacillus subtilis* var. *natto* and *Saccharomyces cerevisiae* fermented liquid feed on growth performance. relative organ weight. intestinal microflora. and organ antioxidant status in Landes geese" Journal of Animal Science, US, vol. 91, No. 2, Feb. 1, 2013 (Feb. 1, 2013), pp. 978-985, 8 pgs.
A. W. Zhang. "Effects of Graded Levels of Dietary *Saccharomyces cerevisiae* on Growth Performance and Meat Quality in Broiler Chickens" Jan. 10, 2005 (Jan. 10, 2005), Retrieved from the Internet: https://www.ajas.info/upload/pdf/18_110.pdf [retrieved on Nov. 13, 2018], 5 pgs.
Kanwal Rafique et al. "Effect of dietary supplementation of different levels of *Saccharomyces cerevisiae* on growth performance and hematology in broiler" Indian Journal of Animal Research, India, No. 00, Jan. 30, 2018 (Jan. 30, 2018), 6 pgs. Jean Philippe Marden et al. "A Bioenergetic-Redox Approach to the Effect of Live Yeast on Ruminal pH during Induced Acidosis in Dairy Cow" American Journal of Analytical Chemistry, vol. 04, No. 10, Jan. 1, 2013 (Jan. 1, 2013), pp. 60-68, 9 pgs.
Eric Pinloche et al. "The Effects of a Probiotic Yeast on the Bacterial Diversity and Population Structure in the Rumen of Cattle" PLOS ONE, vol. 8, No. 7, Jul. 2, 2013 (Jul. 2, 2013), p. e67824, 10 pgs.
L Krizova et al. "The effect of feeding live yeast cultures on ruminal pH and redox potential in dry cows as continuously measured by a new wireless device" Czech J. Anim. Sci, Jan. 1, 2011 (Jan. 1, 2011), pp. 37-45, Retrieved from the Internet: http://www.agriculturejournals.cz/publicFiles/33676.pdf [retrieved on Feb. 23, 2015], 9 pgs.

(Continued)

*Primary Examiner* — Felicia C Turner
(74) *Attorney, Agent, or Firm* — Maier & Maier, PLLC

(57) ABSTRACT

An active yeast adapted to weak organic acids and to the use thereof for poultry or cud-chewing animals. Also, a probiotic for poultry or cud-chewing animals, including an active yeast adapted to weak organic acids. Further, the use of such a yeast for improving the zootechnical performances of poultry and to the use thereof in a probiotic and/or food for poultry. Furthermore, the use of such a yeast for improving the physico-chemical and fermentative parameters of the rumen of cud-chewing animals, and to the use thereof in a probiotic and/or food for cud-chewing animals. In addition, a yeast for use in the prevention and/or the treatment of digestive disorders in cud-chewing animals and particularly in the prevention of acidosis in cud-chewing animals.

9 Claims, No Drawings

(56) References Cited

OTHER PUBLICATIONS

Daniel Sauvant et al. "Approche quantitative de l'acidose chez les ruminants", Jan. 1, 2015 (Jan. 1, 2015), Retrieved from the Internet: https://hal.archives-ouvertes.fr/hal-01413564/document [retrieved on Sep. 6, 2019] , 8 pgs.
Fernández-Pacheco, Pilar et al., "Potential Probiotic Strains of *Saccharomyces* and Non-*Saccharomyces*: Functional and Biotechnological Characteristics", Journal of Fungi, vol. 7, No. 177, Mar. 2021, https://www.mdpi.com/journal/jof, pp. 1-18.
Red Star® Cream Yeast, Lesaffre Yeast Corporation, 1 page.

* cited by examiner

PROBIOTIC FOR POULTRY OR CUD-CHEWING ANIMALS

FIELD

The present invention relates to the field of probiotics for poultry or ruminants. It relates more particularly to a probiotic and a feed for poultry or ruminants comprising same, to the use of an active yeast adapted to weak organic acids and to such a yeast.

The invention relates even more particularly to the use of said active yeast adapted to weak organic acids or of a probiotic comprising such a yeast, in poultry or in ruminants.

With regard to poultry, said yeast or probiotic is in particular used for improving the zootechnical performances of poultry.

With regard to ruminants, said yeast or probiotic is in particular employed for use in the prevention and/or treatment of digestive disorders of ruminants, and in particular in the prevention of acidosis in ruminants.

BACKGROUND

With Regard to Poultry

For many years, antibiotics which, at non-medicinal doses, have a growth factor effect have been commonly used to improve zootechnical performances in poultry breeding.

However, such routine use is not without consequences, for example on the development of antibiotic resistances on the part of bacteria. Thus, in 2006, the European Union decided to ban the use of antibiotics in poultry as a growth factor, in order to limit the appearance of resistance phenomena.

Producers have therefore sought alternatives to antibiotics. Thus, the use of probiotics in poultry has become widespread. Most probiotics sold for poultry are of bacterial origin, mainly from the *Bacillus* family, given their capacity to sporulate and thus to resist the high heat stresses of poultry feed production.

While it has been noted that yeasts, in particular *Saccharomyces cerevisiae*, can have a positive effect on the growth and performances of porcine and bovine livestock, their impact on the growth and weight gain of poultry has not been demonstrated and was often very limited and not significant.

For example, US2002/0146399 proposes a product that can be added to animal feed, in particular for poultry, comprising sorbic acid and at least one culture of microorganisms having a probiotic activity, such as, for example, a culture of the *Saccharomyces cerevisiae* yeast.

WO97/00017 proposes a probiotic, in particular of use for hens, containing algal meal, active dry yeast and a mineral component, it being possible for the yeast to belong to the *Saccharomyces cerevisiae* species.

In addition, there is at the moment in the European Union no authorization for yeast as a probiotic for poultry.

There is therefore a real need to find effective "yeast probiotics" which make it possible to improve the growth and weight gain performances and the consumption index (CI) of poultry.

The term "yeast probiotic" is intended to mean a probiotic comprising a yeast or else a yeast which has a probiotic function. The "yeast probiotic" can also be denoted "probiotic yeast".

With Regard to Ruminants

Acidosis, which is common in ruminants, constitutes one of the major preoccupations of the modern nutrition of ruminant animals. Indeed, the increase in production potentials have led to food intake with a higher energy content. As a result, the rumen (stomach) of the animals must process increased amounts of fermentable organic matter, and the resulting more intense fermentations lead to a state of acidosis with unfavorable zootechnical effects: negative digestive interactions, degradation of the butterfat content of the milk, pathological digestive and metabolic conditions, etc.

Acidosis can be summarized as a disorder of the acid-base balance due to a drop in pH in the rumen (ruminal pH), which results from the degradation of fermentable carbohydrates, the rapid digestion of which by the bacteria in the rumen produces volatile fatty acids (VFAs) and lactic acid.

Under normal conditions, VFAs and lactic acid are absorbed by the ruminal papillae in order to help the animal produce milk. Acidosis sets in when the production of VFAs and lactic acid exceeds the capacity of the ruminal papillae to absorb them.

In order to counteract this state of acidosis in ruminants, and in particular in dairy cows, various feed additives have been proposed in the literature, including probiotic yeasts. Probiotic yeasts are in fact recognized for their stabilizing role on the ruminal environment. Several studies[1,2] have demonstrated the effect of live yeasts on the ruminal pH even though the latter is highly dependent on the diet and in particular on the very nature of the foods which make up said diet. In high producing dairy cows, the supplementing of the food intake with live yeasts is an advantageous solution for limiting the negative effects of the use of acidogenic diets on the digestion and performances of ruminants.

In addition to the measurement of the ruminal pH, the measurement of the ruminal oxidation-reduction potential (redox potential) ($E_h$ in mV) has proved to be a key tool for understanding the method of action of live yeasts[3]. The redox potential is a physico-chemical parameter of interest for understanding not only how the rumen works, but also the ruminal action of the probiotic yeast. It has thus been shown in the literature[4] that the regulation of the ruminal $E_h$ by live yeasts is particularly effective when the risk of rumen dysfunction is sufficiently high[4].

However, there is still at the current time the need to find effective solutions for preventing and/or treating acidosis in ruminants.

SUMMARY

The inventors have developed and established new active yeasts with particular properties, in the sense that they are in particular adapted to weak organic acids.

Thus, according to a first aspect, the present invention relates to these new active yeasts adapted to weak organic acids.

According to a second aspect, the invention relates to the use of these adapted active yeasts in poultry or in ruminants.

According to another aspect, the invention relates to a probiotic for poultry or for ruminants, characterized in that it comprises an active yeast adapted to weak organic acids.

The inventors have also established a feed for poultry or for ruminants comprising the probiotic according to the invention.

According to another aspect, the present invention relates to the use of an active yeast adapted to weak organic acids, for improving the zootechnical performances of poultry.

For the purposes of the present invention, the expression "improvement in the zootechnical performances of poultry" is intended to mean an improvement in the growth and weight gain performances and the consumption index (CI) of poultry.

According to another aspect, the present invention relates to an active yeast adapted to weak organic acids or a probiotic comprising same, for use in the prevention and/or treatment of digestive disorders of ruminants, and in particular the prevention of acidosis in ruminants.

According to another aspect, the present invention relates to the use of an active yeast adapted to weak organic acids in a feed for poultry or for ruminants.

Advantageously, the use of an adapted yeast or of a probiotic according to the invention makes it possible to avoid the addition of enzymes to the feed.

DETAILED DESCRIPTION

A subject of the present invention is a *Saccharomyces cerevisiae* active yeast adapted to weak organic acids, characterized in that it is derived from a strain chosen from the strains deposited at the CNCM [French national microorganism culture collection], respectively under number I-4407 on Dec. 2, 2010, numbers I-5128, I-5129, I-5130 and I-5131 on Aug. 31, 2016, and numbers I-5222 and I-5223 on Aug. 30, 2017, and in that the ratio between the activity according to the A1 test of said adapted active yeast derived from a strain chosen from I-4407, I-5128, I-5129, I-5130, I-5131, I-5222 and I-5223, and the activity according to the A1 test of the non-adapted active yeast derived from the same strain chosen from I-4407, I-5128, I-5129, I-5130, I-5131, I-5222 and I-5223, is greater than or equal to 1.

The term "yeast" denotes yeasts obtained by culturing a yeast strain.

The culturing of the yeast strain is carried out in a culture medium suitable for the growth of the yeast strain.

Those skilled in the art are capable of determining what is the composition of a culture medium suitable for a given yeast strain according to the protocol described in the reference book "Yeast technology" by Gerald Reed and Tilak W. Nagodawithana (ISBN 0-442-31892-8) on pages 284 to 293.

A method for culturing a strain and for obtaining a yeast adapted to a weak organic acid is described in example 1.

The term "active yeast", which is synonymous with live yeast, denotes a population of yeast cells which are metabolically active.

The expression "active yeast . . . derived from a strain" is intended to mean a yeast obtained by culture and adaptation of a strain.

The expression "active yeast adapted to weak organic acids" is intended to mean a yeast of which the tolerance to a given weak organic acid is increased by virtue of a previous exposure to this acid (Warth, 1988, Appl. Environ. Microbiol., 54 (8): 2091-2095). The growth and the fermentative capacity of the adapted yeast are thus not inhibited when the yeast is in the presence of a weak organic acid for at least the second time.

For the purposes of the present invention, the terms "active yeast adapted to weak organic acids", "yeast adapted to weak organic acids", "adapted yeast", "adapted active yeast" have the same meaning.

The term "weak organic acids" is intended to mean organic acids as such and the salts thereof. They are chosen from the group comprising propionic acid, benzoic acid, acetic acid, butyric acid, citric acid, formic acid, fumaric acid, lactic acid, malic acid and sorbic acid, and salts thereof, in particular the calcium or sodium salts.

By way of more particular examples, mention will be made of yeasts adapted to the salts of propionic or benzoic acid, and preferably to calcium propionate or to sodium benzoate.

A method for obtaining a yeast adapted to a weak organic acid is described in example 1, based on the method described in U.S. Pat. No. 4,318,991.

The adaptation of the yeasts according to the invention to the presence of a weak organic acid is more particularly carried out during the final hours of their final multiplication stage, by addition of 0.1 g to 10 g of weak organic acid and/or salts thereof, per liter of culture medium.

According to one particular embodiment of the invention, the *Saccharomyces cerevisiae* active yeast is more particularly *Saccharomyces cerevisiae* var. *boulardii* also called *Saccharomyces boulardii*.

Advantageously, a subject of the present invention is an adapted active yeast, or a probiotic comprising same, of which the ratio of the activity according to the A1 test (described below) between an "adapted" yeast and a non-adapted yeast is greater than or equal to 1. Thus, according to the present invention, the active yeast selected is an active yeast, of the *Saccharomyces* genus, which is characterized by a ratio of the activity according to the A1 test between this selected "adapted" active yeast and the non-adapted yeast, as follows:

Activity of the Adapted Yeast According to the A1 Test

Activity of the non-adapted yeast according to the A1 test greater than or equal to 1.

Said A1 test corresponds to the following protocol:
the volume of $CO_2$ given off by the active yeast is measured for 2 hours with the Burrows and Harrisson fermentometer according to the standard method described on pages 579 to 584 of the reference book "Guide pratique d'analyses dans les industries de céréales" ["Practical guide to analyses in cereal industries"] coordinated by B. Godon and W. Loisel (published by Lavoisier—Tec & Doc—1997—ISBN. 2-7430-0123-2-2nd edition) using the following adapted procedure:
(a) weight out batches of 20 g of flour, the flour being a soft wheat flour having a Hagberg falling time of 200 to 300 seconds (as defined on pages 680 and 681 of the abovementioned reference book), and place them in dry clean tubes, then add 2 g of sucrose to each of the tubes and incubate these tubes in the rack of the water bath, which is at 30° C., for at least 30 minutes before beginning the test;
(b) take the equivalent of 1.066 g of yeast solids as yeast sample;
(c) prepare the diluted yeast samples in 100 ml of distilled water (the dry yeast method is described on page 583 of said reference book) and add 0.5 ml of acetic acid at 6.6% (w/v) just before adjustment to 100 ml;
(d) pipet the 15 ml of the well-mixed diluted sample that are required for the mixing, these 15 ml providing 1.066 g×0.15=0.160 g of yeast solids; and for the rest follow the instructions of the procedure described in the reference book, performing the measurement over the course of 2 hours.

In order to take into account the effect of drying on the activity of the yeast, the activity of the active yeast according to the A1 test is defined as follows:

the yeast tested is in dry form, i.e. at a solids content of at least 90%, its activity corresponds to the volume of $CO_2$ measured.

According to another particular embodiment of the invention, the yeast adapted to weak organic acids, preferably included in a probiotic for poultry or ruminants, is obtained by culture and adaptation of a *Saccharomyces cerevisiae* strain chosen from the strains deposited with the Collection Nationale de Cultures de Microorganismes [French national microorganism culture collection], 25 rue du Docteur Roux 75724 Paris cedex 15, respectively under numbers CNCM I-5128, I-5129, I-5130 and I-5131 on Aug. 31, 2016, under numbers CNCM I-5222 and I-5223 on Aug. 30, 2017, and under number CNCM I-4407 on Dec. 2, 2010.

The inventors have in fact discovered, surprisingly, that yeasts that have undergone a process of adaptation to weak organic acids during their culture are more effective in poultry or in ruminants than yeasts that have not undergone this process.

These "adapted" yeasts thus make it possible in particular to improve the growth and weight gain performances and the feed consumption conversion index relative to the weight gain of the poultry.

The expression "feed consumption conversion index relative to the weight gain" of the poultry is intended to mean the consumption index of the poultry. The consumption index (CI) is the amount of feed ingested (in kilograms) by a poultry bird in order to take on 1 kilogram of live weight.

Surprisingly, in ruminants, the adapted active yeasts of the invention make it possible in particular to improve the regulation of physicochemical parameters of the rumen, such as the pH or the redox potential, and thus to prevent and/or treat acidosis in ruminants.

According to another particular embodiment of the invention, the yeast adapted to weak organic acids is in dry form.

The term "dry yeast" is intended to mean any yeast having a solids content greater than 90%.

Active dry yeast is a live yeast, dried so as to preserve its fermentative capacity and to give it a very long shelf life. Said active dry yeast has a high content of live yeast cells and can be in various forms, for example in the form of spherules, of granules or of powder, all these forms having an average water content of between 4 and 8%.

The drying is carried out according to any method known to those skilled in the art and compatible with cell viability, that is to say make it possible to preserve a high content of live cells. Those skilled in the art also know that, depending on the type of drying carried out, the content of live cells is more or less high, and the performances in the A1 test can be affected.

The weight of solids is determined by conventional methods known to those skilled in the art.

According to yet another embodiment of the invention, the adapted active yeast is in the form of granules, of microspherules or of meal, or in water-dispersible form.

Another subject of the present invention is a probiotic comprising an active yeast adapted to weak organic acids, as defined above.

The term "probiotic" is intended to mean living microorganisms which, when they are ingested in sufficient amount, exert positive effects on the health, beyond the conventional nutritional effects.

The probiotic as defined above comprises at least 90% by weight of solids of the adapted active yeast.

The probiotic of the invention is more particularly a probiotic for poultry or for ruminants. According to another aspect, the present invention relates to a feed for poultry or ruminants comprising the probiotic described above.

The probiotic and the feed for poultry or ruminants according to the invention can also comprise one or more ingredients other than said adapted active yeast, such as in particular vitamins, dietary minerals, trace elements, dietary enzymes, acidifying agents, plant extracts, yeast walls and dietary fats, and also, where appropriate, other microorganisms with a probiotic effect.

According to the knowledge of those skilled in the art of poultry breeding, the growth period of a chicken is from birth to 35-42 days. During this time period, it goes from a mass of 30 to 50 grams to a mass of 2 to 3 kilograms, with a mass which is multiplied 5- to 6-fold over the course of 10 days. Its food, in terms of amount, is preferentially fixed as a function of its age.

According to one particular embodiment of the invention and on this basis of weight of the poultry, the animal receives between $10^6$ and $10^{11}$ CFU of active yeast adapted to weak organic acids per kilogram of feed per day, preferably between $10^9$ and $10^{11}$ CFU/kg of feed/day, and even more preferably between $10^9$ and $10^{10}$ CFU/kg of feed/day.

The term CFU means colony forming unit, one CFU corresponds to one colony.

According to another aspect, the invention relates to a method for improving the zootechnical performances of the animal, in particular for improving the growth and weight gain performances and the consumption index of the poultry, consisting in providing the animal with an active yeast adapted to weak organic acids, in particular between $10^6$ and $10^{11}$ CFU of active yeast adapted to weak organic acids per kilogram of feed and per day, preferably between $10^9$ and $10^{11}$ CFU/kg of feed/day, and even more preferably between $10^9$ and $10^{10}$ CFU/kg of feed/day.

According to another aspect, the invention relates to the use of an active yeast adapted to organic acids for improving the zootechnical performances of poultry.

The term "zootechnical performances" is intended to mean the growth performances, the mass or weight gain of the animal, the consumption index, and the reproduction parameters of the animals.

It has in fact been noted that the use of an adapted yeast in poultry makes it possible to increase the weight gain and the amount of feed ingested and to improve the feed consumption index relative to the weight gain, in particular in growing poultry.

A subject of the invention is more particularly the use of an adapted active yeast as defined above or of a probiotic as defined above, in poultry, in particular for improving the growth and weight gain performances and the consumption index (CI) of poultry.

A subject of the invention is also the use of an adapted active yeast as defined above or of a probiotic as defined above, in ruminants.

More particularly, such a use in ruminants makes it possible to act on the physicochemical parameters of the rumen, such as the pH or the redox potential, but also on the fermentative parameters, such as the content of VFAs present in the rumen.

According to one advantageous embodiment of the invention, the use of the adapted active yeast makes it possible to maintain and/or reestablish the pH of the rumen at a value greater than or equal to $5.8^2$.

According to another advantageous embodiment, the use of the adapted active yeast of the invention makes it possible to maintain and/or reestablish the redox potential of the rumen at a value ranging from −200 mV to −150 mV.

The pH and redox potential values described above correspond to those obtained by the method of measurement described in example 4 below.

According to yet another advantageous embodiment, the use of the adapted active yeast of the invention makes it possible to increase the VFA concentration in the rumen.

By acting on the physicochemical or fermentative parameters as described above, the adapted active yeast of the invention advantageously makes it possible to act on the acidosis of ruminants, and more particularly to prevent ruminal acidosis in ruminants.

A subject of the invention is thus also an adapted active yeast as defined above or a probiotic as defined above, for use in the prevention and/or treatment of digestive disorders of ruminants, and more particularly in the prevention or acidosis in ruminants.

According to another aspect, the invention relates to a method for preventing and/or treating acidosis in ruminants, consisting in providing the animal with an active yeast adapted to weak organic acids, in particular in an amount ranging from 0.5 g to 50 g of adapted active yeast per animal and per day, preferably from 1 g to 10 g of adapted yeast per animal and per day.

According to another aspect, the invention relates to the use of an active yeast adapted to organic acids in a probiotic and/or in a feed for poultry or ruminants, as described above.

A subject of the invention is the use of an adapted active yeast as defined above or of a probiotic as defined above, in a feed for poultry or for ruminants.

According to another particular embodiment of the invention, the active yeast adapted to organic acids and/or the probiotic are used in a form suitable for use in a dietary matrix, said matrix being for example granules, meal or drinking water.

The yeast adapted to weak organic acids and/or the probiotic are for example in the form of granules or of meal when they are mixed with the feed and in water-dispersible form when they are mixed with drinking water.

According to another aspect, the invention relates to the use of an active yeast adapted to weak organic acids, wherein the animal, in particular a poultry bird weighing between 30 and 3000 g, receives between $10^6$ and $10^{11}$ CFU of active yeast adapted to weak organic acids per kilogram of feed per day, preferably between $10^9$ and $10^{11}$ CFU of feed/day, and even more preferably between $10^9$ and $10^{10}$ CFU/kg of feed/day.

The probiotic, the feed, the use of the adapted yeast and the adapted yeast according to the invention are in particular of use in the field of the breeding of poultry chosen from the group comprising:
- farmyard birds and gallinaceous birds, and in particular hens, including chicks, roosters and cockerels, capons and laying hens, turkey hens and turkey cocks,
- anseriformes and in particular male ducks, female ducks, geese and pheasants, guinea-fowl, quails and partridges,
- the Columbidae, in particular pigeons,
- ratites, in particular ostriches, emus and kiwis.

According to another aspect, the invention relates to the use of an active yeast adapted to weak organic acids, wherein the ruminant receives from 0.5 g to 50 g of active yeast adapted to weak organic acids per day, and preferably between 1 g and 10 g of yeast per day.

The probiotic, the feed, the use of the adapted yeast and the adapted yeast according to the invention are in particular of use in the field of the feeding of ruminants of the bovid and camelid family.

Bovids (Bovidae) comprise several subfamilies, including in particular bovines (which include cattle) and the caprinae (which encompass members of the goat family and members of the sheep family).

Camelids (Camelidae) are artiodactyl mammals which encompass, for example, the dromedary, the camel or the llama.

The probiotic according to the invention comprises at least 90% by mass of solids of the selected "adapted" active yeast.

The present invention will be illustrated by means of the implementation examples which follow, it being understood that said examples are in no way limiting in scope.

EXAMPLES

Example 1: Method for Obtaining a Dry Active Yeast Adapted to a Weak Organic Acid 1.1. "Standard" Culture Method The yeasts can be obtained by culturing on beetroot molasses or cane molasses for example, according to the fed-batch method.

The culture method comprises a succession of fermentation steps as described on pages 284 to 293 of the reference book "Yeast technology" by Gerald Reed and Tilak W. Nagodawithana (ISBN 0-442-31892-8).

1.2. Method for Inducing an Adaptation

The method for inducing the adaptation to a weak organic acid corresponds to the standard culture method above, modified as follows according to the steps below:

1. acidification: 2 to 3 h before the end of the culture (cf. above, the "standard" culture method) and before the adaptation phase, the pH of the culture medium is adjusted to a value of between 4.0 and 5.5 and is maintained until the end of the adaptation phase, for example with sulfuric acid;
2. adaptation: an amount of weak organic acid or of its associated salt is added to the culture medium so as to obtain between 1500 and 3000 ppm (parts per million) of weak organic acid by weight in the culture medium. The weak acid addition dose is linked to the composition of the weak acid or its associated salt that is used. The culture medium is devoid of buffer.

Those skilled in the art will know how to adjust the pH and the amount of weak organic acid to be used without this involving an excessive burden.

1.3. Drying

The active dry yeasts selected, that is to say the dry yeasts having a high content of living yeast cells, obtained by drying according to a technique known to those skilled in the art, in order to obtain a solids content greater than 90%.

Example 2: Measurement of the Ratio of the Activity According to the A1 Test Between an Adapted Yeast and a Non-Adapted Yeast The yeasts a and b correspond to 2 different batches a and b of the strain of non-adapted yeast deposited with the CNCM on Aug. 31, 2016, under number I-5131, that is to say a yeast that has not undergone the adaptation method described in example 1.2.

The yeast that has been "adapted", according to the method described in examples 1.1 and 1.2, used in the A1 test corresponds to 2 different batches a and b of the same yeast strain I-5131.

The A1 test is that described above.

Results of the A1 Test:

TABLE 1

| Strains | Activity (ml of $CO_2$) |
|---|---|
| I-5131 non-adapted (a) | 103 |
| I-5131 non-adapted (b) | 113 |
| I-5131 adapted (a) | 106 |
| I-5131 adapted (b) | 132 |

Ratio of the Activity According to the A1 Tests Between the Adapted Yeast I-5131 and the Non-Adapted Yeast I-5131:

TABLE 2

| Batches | Ratio |
|---|---|
| Batch (a) | 1.029 |
| Batch (b) | 1.168 |

Conclusion: The adapted yeasts used according to the invention thus have a ratio greater than 1.

Other tests were carried out, all batches included, on respectively:
- batches of non-adapted yeasts derived from the I-5131 strain,
- batches of yeasts adapted to propionic acid, derived from the I-5131 strain.

The results obtained are given in table 3 below:

| Strains | Activity (ml of $CO_2$) (mean) | Standard error | Lower limit | Upper limit |
|---|---|---|---|---|
| I-5131 non-adapted | 109.571 | 2.173 | 105.140 | 114.003 |
| I-5131 adapted to propionic acid | 121.667 | 1.659 | 118.282 | 125.051 |

Conclusion: The adapted active yeasts used according to the invention have a ratio greater than 1, all batches taken into account.

Other tests were carried out, all batches taken into account, on respectively:
- batches of non-adapted yeasts derived from the I-5129 strain,
- batches of yeasts adapted to propionic acid, derived from the T-5129 strain.

The results obtained are given in table 4 below:

| Strains | Activity (ml of $CO_2$) (mean) |
|---|---|
| I-5129 non adapted | 112.3 |
| I-5129 adapted to propionic acid | 126.3 |

Conclusion: The adapted active yeasts used according to the invention have a ratio greater than 1, all batches taken into account.

Example 3: Tests on an "Adapted" Yeast, for Feeding Poultry

The adapted active dry yeasts exhibit surprising advantageous properties in the poultry farming field.

These surprising advantageous properties are illustrated by the results of the following test on chicks.

Conventionally, according to the knowledge of those skilled in the art in poultry breeding, the feed used for chicks is a thickening wheat, in other words a wheat of medium to poor quality. This represents a nutritional challenge, in other words a type of stress. According to the knowledge of those skilled in the art, one of the means for improving the digestibility of such a wheat is the addition of enzymes. In the context of the present invention, there is no addition of enzymes, which represents a not insignificant advantage in terms of cost.

In this test, the results obtained by means of the addition of a probiotic according to the invention to a meal feed for chicks are compared with the results obtained with this feed without additive, and with a mixture of this feed with the same active dry yeast that is non-adapted.

Chicks

The test was carried out over a period of from 1 to 21 days on a population of chicks corresponding to the following criteria: ROSS chicks 1 day old at the start of the test.

Composition of the Meal Feed for Chicks

The meal feed consists mainly of wheat and corn without anti-thickening enzymes (as explained above) according to the following composition:

TABLE 5

| Ingredient | Amount (%) |
|---|---|
| Wheat | 40.0 |
| Corn | 39.8 |
| Soya meal | 16.6 |
| DL methionine | 0.1 |
| Calcium diphosphate | 1.5 |
| Calcium carbonate | 1.0 |
| Vitamins-minerals premix | 0.6 |
| Salt | 0.4 |

The composition of the various mixtures for chicks is given in table 6 below.

TABLE 6

| Mixture tested | Additive added per g of meal feed |
|---|---|
| Control | / |
| Non-adapted yeast mixture | 800 g/T i.e. $10^7$ CFU/g of feed of the active dry yeast I-5128 |
| Adapted yeast mixture | 800 g/T i.e. $10^7$ CFU/g of feed of the adapted active dry yeast I-5128 |

Test Protocol

The chick population was randomly divided into 2 replicates of 3 batches of 6 cages each containing 20 chicks, each chick batch receiving a mixture to be tested according to table 5.

Starting from the first day, the chicks of each group were fed ad libitum with the mixture corresponding to the test batch. The chicks were also given water ad libitum.

No other food source was made available to the chicks.

The amount of meal consumed by each group was measured.

At various times during the test, the live weight of the chicks was measured, respectively on D0 (1-day-old chicken), D+7 days, D+14 days, D+21 days.

Results:

The results of the test, at D+21 days, are given in table 7, in which:

FI-x means the total mean amount (in g) of mixture consumed per chick of the given group after x days, in the case in point here FI-21, after 21 days;

LW-x means the mean live weight (in g) of the chicks of the given group after x days, in the case in point here LW-21, after 21 days;

FCR-x means the ratio between, on the one hand, the mean live weight gain (in g) of the chicks of the given group after x days and, on the other hand, the total mean amount of mixture consumed per chick of said group after x days, in the case in point here FCR-21, after 21 days.

|  | Control | I-5128 | I-5128 adapted | SEM | ANOVA (P) |
|---|---|---|---|---|---|
| Initial LW | 40 | 40 | 40 | | |
| LW-21 | 516.2a | 514.6a | 545.2b | 6.9 | 0.036 |
| FI-21 | 820.9 | 814.3 | 833.6 | 7.8 | 0.551 |
| FCR-21 | 1.67a | 1.65a | 1.60b | 0.01 | 0.021 |

SEM means standard error of the mean.

ANOVA Means ANalysis of VAriance

The different letters a, b used indicate whether or not the values are statistically different. Thus, the results are not significantly different when the same letter is reported ($p>0.05$).

Conclusion: The results show that the supplementation with an adapted yeast significantly improves the growth (LW21) and feed conversion (FCR21) results for the chicks, whereas the non-adapted yeast has no effect.

Example 4: Influence of an Adapted Active Yeast on the Physicochemical and Fermentative Parameters of Ruminants Description of the Protocol/Methodology The in vitro tool chosen in this example is the "Dual-Flow" method which has demonstrated its ability to effectively imitate fermentation in the rumen[6,7].

In a conventional double-flow system, the pH is kept constant using acid and base. In this example, the pH is controlled only by the amount and the buffering capacity of the artificial saliva injected into the fermentation reactors, so that the physicochemical parameters of the kinetics evolve in the same way as if they were measured in the rumen.

In the dual-flow fermentation system used to measure the parameters of the invention, the degree of liquid dilution and the degree of solids dilution can be configured by the user to mimic a rumen in a situation of weak or strong acidosis.

It is composed of twenty-four 1 L bioreactors equipped with 2 side arms to discharge the solid particles and to feed and pump the liquid. Each bioreactor has 4 inlets, namely a saliva feed, a gas outlet, a pH probe and a redox probe.

The temperature is maintained at 39° C. by incubating the bioreactor containing ruminal fluid in a water bath and the content is stirred using a stirrer.

The pH is maintained with a bicarbonate buffer[8].

The pH and the redox potential ($E_h$) are recorded in real time with a multiple-entry data recorder.

After inoculation, the system is hermetically closed and the anaerobic state is evaluated by measuring the redox potential. The effluents are collected daily.

Lactating cows bearing a cannula at the level of the rumen were sampled and the liquid was collected, filtered through 2 layers of muslin and mixed with an equal volume of bicarbonate buffer under anaerobic conditions.

Each bioreactor is then filled to overflowing while at the same time being subjected to $CO_2$, and inoculated with 15 g of feed composed of corn silage, soya oilcakes, hay and transformed corn.

Each bioreactor is fed (15 g of granules) daily at 9 am to 4 pm.

Initially, the dual-flow experiments are designed in accordance with what is described in Stern et al.[8].

Prior studies reveal that an adaptation to the feed of at least 7 days is required to obtain a stable fermentation scheme.

The live yeast strains I-5129 that were non-adapted and adapted to calcium propionate or to sodium benzoate were evaluated in iso-equivalent CFUs.

The number of CFUs was adjusted to have iso-equivalent CFUs.

Physicochemical parameters such as the pH or the redox potential ($E_h$) were measured and organized on the measurement kinetics established during the sixteenth and seventeenth day of fermentation corrected by the covariate period during the sixteenth and seventeenth day of measurement.

The analysis of the individual and total VFAs was carried out on the fluid from the rumen (ruminal fluid) sampled on the same bases as the pH and redox potential measurements.

Diurnal pH and $E_h$ recordings were carried out during the various phases (stabilization and adaptation phases) by means of the continuous measurement software.

The data were collected and processed by means of the linear mix model using the SPSS software (IL, Chicago) and the fermentation parameters were processed by means of the univariate model.

Each individual fermenter was considered to be an experimental unit.

There were 6 repetitions for each treatment (yeast or no yeast).

The treatments are shown significantly different at $P<0.05$ and the tendencies at $P<0.10$, and also the paired comparison.

Results

In the tables below:

"I-5129 NA" denotes the non-adapted yeast,

"I-5129 Prop" denotes the yeast adapted to calcium propionate,

"I-5129 Benz" denotes the yeast adapted to sodium benzoate.

The control represents a sample of the ruminal fluid without the presence of yeast.

| Rumen pH | | | |
|---|---|---|---|
|  | Control | I-5129 NA | I-5129 Prop |
| pH Mean over the course of 24 hours | 5.62a | 5.60a | 5.84b | a,b: the mean values on one and the same line with one and the same suffix are not statistically different from one another.

The pH effect is notable on the yeast adapted to calcium propionate.

| Rumen redox potential ($E_h$) | | | | |
|---|---|---|---|---|
|  | Control | I-5129 NA | I-5129 Prop | I-5129 Benz |
| $E_h$ (mV) Mean over the course of 24 hours | −163.8b | −166.5b | −172.7a | −172.1a | a,b: the mean values on one and the same line with one and the same suffix are not statistically different from one another.

The redox potential kinetics show a significant drop to lower values with the yeasts I-5129 adapted to propionate and to benzoate relative to the control (−10 mV) and to the non-adapted yeast (−6 mV).

The kinetics of the redox potential $E_h$ for the adapted yeasts showed a significant difference (−6 mV) relative to the non-adapted yeasts.

|  | Control | I-5129 NA | I-5129 Prop |
|---|---|---|---|
| $E_h$ (mV) Mean over the course of 24 hours | −156.8b | −147.5b | −166.0a | a,b: the mean values on one and the same line with one and the same suffix are not statistically different from one another.

The $E_h$ values vary from −147.5 mV to −166.0 mV for the yeasts which are respectively non-adapted and adapted.

Conclusion

The adapted yeasts showed lower redox potential values, which shows that the reducing capacity of the ruminal medium is reinforced.

VFA Concentrations

| VFA concentrations | | | |
|---|---|---|---|
|  | Control | I-5129 NA | I-5129 Benz |
| Total VFA content (mM/L) | 90.4a | 92.4a | 93.7b |

The total VFA concentrations vary from 90.4 mM for the control without yeast to 93.7 mM with the yeast I-5129 adapted to benzoate.

The total VFA concentrations significantly increase with the yeast I-5129 adapted to benzoate (+3.7% or 3.3 mM/L) relative to the control or relative to the non-adapted yeast I-5129 (+1.4% or 1.3 mM/L).

Conclusion:

The yeast I-5129 adapted to benzoate promotes a more reducing ruminal (rumen) medium, which results in a greater VFA content.

LITERATURE REFERENCES

1. Marden, J. P., Julien, C., Monteils, V., Auclair, E., Moncoulon, R., Bayourthe, C., 2008, How does live yeast differ from sodium bicarbonate to stabilize ruminal pH in high yielding dairy cows? J. Dairy Sci. 91, 3528-3535.
2. Desnoyers, M., Giger-Reverdin, S., Bertin, G., Duvaux-Ponter, C., Sauvant, D., 2009, Meta-analysis of the influence of Saccharomyces cerevisiae supplementation on ruminal parameters and milk production of ruminants. J. Dairy Sci. 92(4), 1620-1632.
3. Marden, J. P., Bayourthe, C., Enjalbert, F., Moncoulon, R., 2005, A new device for measuring kinetics of ruminal pH and redox potential in dairy cows. J. Dairy Sci. 88, 277-281.
4. Pinloche, E., McEwan, N., Marden, J. P., Bayourthe, C., Auclair, E., Newbold, C. J., 2013, The effects of a probiotic yeast on the bacterial diversity and population structure in the rumen of cattle. PLoS ONE 8(7): e67824. doi:10.1371/journal.pone.0067824.
5. Huang et al., Analyse quantitative de l'effet des levures vivantes sur le potentiel redox ruminal chez la vache laitiere. Rencontres autour des Recherches sur les Ruminants 23, 41.
6. Busquet M, Calsamiglia S, Ferret A, Cardozo P W, Kamel C (2005) Effects of cinnamaldehyde and garlic oil on rumen microbial fermentation in a dual flow continuous culture. J Dairy Sci 88: 2508-2516.
7. Cerrato-Sanchez M, Calsamiglia S, Ferret A (2008) Effect of the magnitude of the decrease of rumen pH on rumen fermentation in a dual-flow continuous culture system. J Anim Sci 86: 378-383.
8. M. D. Stem, H. W. Hoover (1990). The dual flow continuous culture system. Proc. Continuous Culture Fermenters: Frustration or fermentation, Northwest ADSA-ASAS Regional meeting, Chazy, N.Y. (1990), pp. 17-32

The invention claimed is:

1. A method for improving the growth and weight gain performances and the consumption index (CI) of poultry, comprising administering to a poultry animal an effective amount of a Saccharomyces cerevisiae active yeast adapted to a weak organic acid chosen from propionic acid and its salts, wherein:
    said adapted Saccharomyces cerevisiae active yeast is obtained by the adaptation of a Saccharomyces cerevisiae active yeast derived from a strain chosen from the strains deposited at the CNCM under number I-5128 and I-5131 on Aug. 31, 2016, to the presence of a weak organic acid carried out during the final hours of a final multiplication stage by addition of 0.1 g to 10 g of weak organic acid and/or salts thereof, per liter of culture medium, so as to obtain between 1500 and 3000 ppm of weak organic acid by weight in the culture medium;
    a ratio of a volume of $CO_2$ given off for 2 hours of culture from said adapted Saccharomyces cerevisiae active yeast derived from the strain chosen from I-5128 and I-5131 to a volume of $CO_2$ given off for 2 hours of culture from a non-adapted Saccharomyces cerevisiae active yeast derived from the strain chosen from I-5128 and I-5131 is greater than or equal to 1; and
    said adapted Saccharomyces cerevisiae active yeast has an increased tolerance to a weak organic acid by virtue of a first exposure to said weak organic acid during the final multiplication stage such that said adapted Saccharomyces cerevisiae active yeast has a growth and a fermentative capacity of that are not inhibited when said adapted Saccharomyces cerevisiae active yeast is in the presence of said weak organic acid for at least a second exposure.

2. The method as claimed in claim 1, wherein the administration of the adapted Saccharomyces cerevisiae active yeast is made via a feed comprising the adapted Saccharomyces cerevisiae active yeast or a probiotic comprising the adapted Saccharomyces cerevisiae active yeast.

3. The method as claimed in claim 1, wherein the poultry receives between $10^6$ and $10^{11}$ CFU of adapted active yeast per kilogram of feed per day.

4. The method as claimed in claim 1, wherein the adapted Saccharomyces cerevisiae active yeast is adapted to calcium or sodium salts of propionic acid.

5. The method as claimed in claim 1, wherein the adapted Saccharomyces cerevisiae active yeast is adapted to calcium propionate.

6. The method as claimed in claim 1, wherein the adapted Saccharomyces cerevisiae active yeast is in dry form.

7. The method as claimed in claim 1, wherein the adapted Saccharomyces cerevisiae active yeast is in the form of granules, microspherules, meal, or in a water-dispersible form.

8. The method as claimed in claim 1, wherein the adapted *Saccharomyces cerevisiae* active yeast is in a feed for poultry.

9. The method as claimed in claim 1, wherein the poultry is a poultry receives between $10^9$ and $10^{10}$ CFU of adapted *Saccharomyces cerevisiae* active yeast per kilogram of feed per day.

* * * * *